United States Patent [19]
Jaeger et al.

[11] Patent Number: 5,273,757
[45] Date of Patent: Dec. 28, 1993

[54] APPARATUS FOR THE DELIVERY OF SUBSTANCES, PROCESSES FOR THE PRODUCTION THEREOF AND USE THEREOF

[75] Inventors: Halvor Jaeger, Neu-Ulm; Hans-Rainer Hoffmann, Neuwied; Reinhold Meconi, Neuwied; Robert-Peter Klein, Neuwied, all of Fed. Rep. of Germany

[73] Assignee: LTS Lohmann Therapie-Systeme GmbH & Co. KG, Neuwied, Fed. Rep. of Germany

[21] Appl. No.: 883,911

[22] Filed: May 12, 1992

Related U.S. Application Data

[63] Continuation of Ser. No. 751,645, Aug. 26, 1991, abandoned, which is a continuation of Ser. No. 566,856, Aug. 10, 1990, abandoned, which is a continuation of Ser. No. 353,656, Jun. 9, 1989, abandoned.

[30] Foreign Application Priority Data

Sep. 1, 1987 [DE] Fed. Rep. of Germany ....... 3729165
Dec. 23, 1987 [DE] Fed. Rep. of Germany ....... 3743945

[51] Int. Cl.$^5$ .................................................. A61F 13/02
[52] U.S. Cl. ..................................... 424/448; 424/449
[58] Field of Search .................... 424/448, 449, 465

[56] References Cited

U.S. PATENT DOCUMENTS 4,668,232 5/1987 Cordes ................................ 604/897
4,840,796 6/1989 Sweet .................................. 424/448

Primary Examiner—Paul R. Michl
Assistant Examiner—D. Gabrielle Phelan
Attorney, Agent, or Firm—Kalish & Gilster

[57] ABSTRACT

The invention relates to an apparatus for the release or delivery of substances from hot melt contact adhesives with uniform or irregular distribution of the substances, the hot melt contact adhesive having a processing temperature between 40° and 80° C., preferably between 40° and 60° C. and in particularly preferred manner between 40° and 55° C.; a process for the production of this apparatus; as well as the use of this apparatus in human and veterinary medicine, diagnosis or cosmetics.

25 Claims, 1 Drawing Sheet

APPARATUS FOR THE DELIVERY OF SUBSTANCES, PROCESSES FOR THE PRODUCTION THEREOF AND USE THEREOF

This application is continuation of application Ser. No. 07/751,645, filed Aug. 26, 1991, now abandoned, or which is a continuation of application Ser. No. 07/566,856 filed Aug. 10, 1990, now abandoned, which is a continuation of application Ser. No. 07/353,656, filed Jun. 9, 1989, now abandoned.

BACKGROUND AND SUMMARY OF THE INVENTION

The invention relates to an apparatus for the release of substances from hot melt pressure sensitive adhesives, with a non-uniform or irregular distribution of the substances, process for the preparation thereof and the use thereof.

Typical representatives of such apparatus are active substance-containing plasters, indicator systems, perfume-releasing apparatuses and the like, where they are frequently more particularly used in the medical field for the controlled or uncontrolled release of substances. Particular significance has been attached to the controlled apparatuses in the form of transdermally controlled systems. It is already known in connection therewith to apply an active substance-containing layer from the melt. EP-OS 0177893 discloses a nonadhesive cellulose ether gel which can be applied from the melt and in which active substances can be distributed. This gel is hot processed and is nonadhesive. DE-OS 32 22 800 discloses a transdermal system, in which active substance packed in microcapsules is present in a thermally shapeable, adhesive matrix material, which is applied from the melt.

For temperature-sensitive active substances with a low melting point or which can be easily decomposed, attempts have also been made to produce nonadhesive active substance-containing matrixes at ambient temperature. For example, it is stated in U.S. Pat. No. 4,379,454 (Campbell et al.) that an active substance solution brought to a desired viscosity value by means of gelling agents at ambient temperature can be used for the active substance layer. It is known from U.S. Pat. No. 4,559,222 (Enscore et al.) to use a mixture of mineral oil/polyisobutylene and colloidal silicon dioxide prepared at ambient temperature as a viscous active substance layer for oil-soluble active substances, whereby said layers can also be made in pressure sensitive adhesive manner. DE-OS 32 22 800 (ALZA) describes an active substance layer from an active substance solution thickened by means of a rheological agent, such as cellulose, a polysaccharide or a silicon compound, which is nonadhesive and is also suitable for rapid active substance release.

U.S. Pat. No. 3,923,939 discloses shaping active substances, such as tetracycline, in an ethylene-vinyl acetate copolymer layer by melt pressing. In EP-OS 86 468 an oral antidiabetes sulphonyl urea derivative in a nonadhesive hot melt mass with a melting point of 30° to 90° C. is filled into capsules in predetermined doses from the melt. U.S. Pat. No. 3,957,966 discloses that active substances can be processed in nonadhesive hot melt masses.

It is known from DE-OS 30 07 363 to use a pressure sensitive adhesive mixture of a thermoplastic elastomer, preferably a block polymer of general formula A—B—A, a tackifying resin with oil or higher fatty acids and active substance for producing a simple transdermal system. The pressure sensitive adhesive mixture described therein is only suitable for relatively temperature-resistant active substances, which are able to withstand temperatures of 120° C. and higher. U.S. Pat. No. 3,699,963 discloses mixing oxytocin with pressure sensitive adhesive for producing a transdermal therapeutic system and shaping thereof at a temperature above 90° C. The thus produced transdermal systems are inexpensive to produce and ensure a constant active substance transfer via the whole-area adhesion of the system to the skin.

The prior art processes for producing such systems are not suitable for transdermal systems containing temperature-sensitive substances, such as scopolamine. Therefore hitherto pressure sensitive adhesive active substance layers with temperature sensitive active substances have preferably been formed from the solution and the solvent evaporated.

The use of solvents in the preparation of active substance-containing adhesive layers is disadvantageous for several reasons. The preparation of the solutions requires at least one additional, complicated process stage. It leads to high technical effort and expenditure in connection with the handling of the solvents, whilst in addition for medical purposes it is necessary to use extremely pure and therefore expensive solvents, in order to ensure a corresponding freedom from residue in the apparatus for the dissolving of the adhesive or its starting materials. Another problem is to achieve freedom from solvent in the apparatus, for which purpose it is necessary to use expensive drying sections and suction installations. Costs are additionally incurred through the recovery or separation of the solvent, in order to avoid pollution of the environment. An additional risk is caused by the flammability of most solvents. In addition, most organic solvents are harmful to the human organism, so that complicated and costly protective measures must be taken for personnel working in the plant.

The problem of the present invention is therefore to avoid the aforementioned disadvantages of such apparatuses and processes according to the prior art.

According to the invention this problem is solved by an apparatus for the release of active substances from hot melt pressure sensitive adhesives with a non-uniform or regular distribution of the substances, in which the hot melt pressure sensitive adhesive has a processing temperature between 40° and 80° C., preferably between 40° and 60° C. and in particularly preferred manner between 40° and 55° C.

This makes it possible to work without solvents at low temperatures, so that there is a considerable saving on materials, a speedier production of the apparatus without the time consuming drying stages, as well as a production of the inventive apparatuses which leads to less pollution of the environment, which inter alia leads to a considerably less expensive and also solvent-free product.

An inventive process for the production of an inventive apparatus involves the continuous or discontinuous application of melted hot melt pressure sensitive adhesive containing the substance to be released at a hot melt pressure sensitive adhesive temperature between 40° and 80° C., preferably between 40° and 60° C. and in particularly preferred manner 40° to 55° C. to a carrier and optionally application of the protective layer material.

A further inventive process involves the continuous or discontinuous application of melted hot melt pressure sensitive adhesive containing the substance to be released at a hot melt pressure sensitive adhesive temperature between 40° and 80° C., preferably between 40° and 60° C. and in particularly preferred manner between 40° and 55° C. to a protective layer material and optionally application of the carrier.

When using highly volatile and/or thermally unstable active substances to be released, the following measures are appropriate for processing purposes:

A. working at very low temperatures,
B. increasing the external pressure in order to reduce evaporation,
C. saturation of the vapour chamber over the melt with the vaporous substance and
D. working with a minimum volatile substance quantity in the melt.

Obviously these measures, such as e.g. working in an encapsulated plant, are limited by the rules known to the Expert through the intended use of the apparatus to be produced and also the material circumstances.

The inventive apparatuses, particularly transdermal systems can e.g. be used for local or systemic, transdermal active substance administration in human or veterinary medicine or cosmetics and are preferably used for the release of temperature-sensitive and/or highly volatile substances.

Hot melt pressure sensitive adhesive is here understood to mean any pressure sensitive adhesive, which is adquately liquid when hot to permit problem free applicaction at a temperature above approximately 40° C.

As inventively usable hot melt pressure sensitive adhesives can inter alia be used those which are known to the Expert and such as are inter alia described in DE-OS 15 94 268 (SUN OIL CO.), DE-OS 24 13 979 (E.I. DU PONT DE NEMOURS), DE-OS 24 35 863 (DYNAMIT NOBEL AG), DE-OS 28 00 302 (CIBA GEIGY), EP-A-104 005 (PERSONAL PRODUCTS CO.), JP 6104 2583 and JP 61 281 810, EP-OS 131 460 (EXXON), EP-OS 234 856 (EXXON), EP-OS 185 992 (EASTMAN KODAK), as well as U.S. Pat. Nos. 3,699,963 and 4,358,557 (EASTMAN KODAK) and express reference is made to this prior art to avoid unnecessary repetition.

The basic polymers can be constituted e.g. by polyamides, polyesters, polycaprolactams, polycaprolactone, ethylene-vinyl acetate copolymers (EVA), ethylene-ethylacrylate copolymers (EEA), polyvinylethers, polyacrylate esters, polyvinylacetals, polyvinylacetates, styrene-butadiene block polymers, isoprene block polymers, polyurethanes, ethylcellulose, cellulose acetate-butyrate, synthetic rubbers (e.g. neoprene rubber), polyisobutylene, butyl rubber, acrylonitrile-butadiene copolymers, epoxy resins, melamine resins, phenol-formaldehyde resins and resorcinol-formaldehyde resins and inter alia the following modifying resins can be used: hydrogenated colophony, polymerized colophony, dimerized resin acids, disproportionated colophony, colophony methyl esters, hydrogenated colophony glycerol esters, hydrogenated colophony methyl esters, pentalesters, hydrogenated colophony triethyleneglycolesters, hydroabiethyl alcohol and its derivatives, glycerol esters, ditriolesters and pentaesters of resin acids, polymerized colophony pentalesters, dimerized colophony pentalesters, dimerized colophony glycerol esters, esters of maleic acid or phenol-modified colophony, aromatic and aliphatic hydrocarbon resins, hydrogenated resins, polyterpene resins, modified terpene resins, waxes, low molecular weight polyethylene and polypropylene and alkyl-styrene copolymers. To these resins can optionally be added plasticizers, such as e.g. adipic acid esters, phosphoric acid esters, phthalic acid esters, polyesters, fatty acid esters, citric acid esters or epoxide plasticizers. It is also possible to admix stabilizers, such as tocopherol, substituted phenols, hydroquinones, pyrocatechols, aromatic amines and optionally also fillers, such as e.g. titanium dioxide, magnesium oxide, zinc oxide and silicon dioxide.

The formation of components of the apparatus having hot melt pressure sensitive adhesive with a processing temperature between 40° and 80° C. can take place by extrusion, pouring, roller application, knife coating, spraying or printing processes.

A limit value for the processability of the hot melt pressure sensitive adhesive in many of these processes is at a viscosity of approximately 80,000 Pa.

If the substrate to be treated with the adhesive, a component of the apparatus, could be damaged by the temperature of the hot-applied adhesive, either by decomposition, reaction or partial melting, it is possible to use a cooled substrate. Cooling can take place by per se known processes, such as the introduction of cold inert gases or contacting with a cooling surface.

The hot melt pressure sensitive adhesive can e.g. be applied in layer form or in individual areas in accordance with a predetermined pattern to the protective layer or the covering material.

As a function of the intended use and e.g. if the substance to be released is to be released through the backing layer, such as can be the case with essential oils, such as fragrances, the hot melt pressure sensitive adhesive can be finished with a carrier permeable with respect to the substance or substances to be released, whilst in the embodiment of the apparatus as a transdermal system, where the substance is only to be delivered to the skin, preference is given to a backing layer which is impermeable for the substance to be delivered.

The inventive process makes it possible to obviate the use of solvent-containing, pressure sensitive adhesive materials in the processing of temperature-sensitive, highly volatile substances, which considerably increases the safety of production, because it is now certain that no toxic solvent residues can remain in the medicinal administration form, as well as bringing about a greatly simplified application process and considerable production cost savings. The process can naturally also be used in advantageous manner for less temperature-sensitive substances, because this also leads to considerable cost savings.

The expression "substances" in connection with the present invention is understood to mean chemical elements, organic and inorganic compounds, which can migrate out of the components containing them in such an apparatus and can thereby bring about a sought effect. Among the uses of the inventive apparatus particulare significance is attached to human and veterinary medicine, a realization of the invention in plaster form being particularly preferred.

Typical substances which can be administered by means of inventively produced apparatuses are: aceclidine, amphetaminil, amphetamine, amylnitrite, apophedrin, atebrin, alprostadil, azulene, arecoline, anethole, amylenehydrate, acetylcholine, acridine, adenosintriphosphoric acid, L-malic acid, alimemazine, allithiamine, allyl isothiocyanate, aminoethanol, apyzine, apiol, azatadine, alprenolol, ethinazone, benzoylperoxide, benzyl alcohol, bisabolol, bisnorephedrine, butacetoluid, benactyzine, campher, colecalciferol, chloralhydrate, clemastine, chlorobutanol, capsaicin, cyclopentamine, clobutinol, chamazulene, dimethocaine, codeine, chloropromazine, quinine, chlorothymol, cyclophosphamide, cinchocaine, chlorambucil, chlorphenesin, diethylethane, divinylethane, dexchlorpheniramine, dinoprostone, dixyrazine, ephedrine, ethosuximide, enallylpropymal, emylcamate, erytroltetranitrate, emetine, enflurane, eucalyptol, etofenamate, ethylmorphine, fentanyl, fluanisone, guajazulene, halothane, hyoscyamine, histamine, fencarbamide, hydroxycaine, hexylresorcinol, isoaminilcitrate, isosorbidedinitrate, ibuprofen, iodine, iodoform, isoaminile, lidocaine, lopirine, levamisole, methadone, methyprylone, methylphenidate, mephenesine, methylephedrine, meclastine, methopromazine, mesuximide, nicethamide, norpseudoephedrine, menthol, methoxyflurane, methylpentinol, metixen, misoprostol, oxytetracaine, oxyprenolol, oxyphenbutazone, oxyquinoline, pinene, prolintane, procyclidine, piperazine, pivazide, phensuximide, procaine, phenindamine, promethazine, pentetrazole, profenamine, perazine, phenol, pethidine, pilocarpine, prenylamine, phenoxybenzamine, resochin, scopolamine, salicyclic acid ester, sparteine, trichloroethylene, timolol, trifluperazine, tetracaine, trimipramine, tranylcypromine, trimethadione, tybamate, thymol, thioridazine, valproic acid, verapamil, as well as other active substances which can be taken up through the skin. Obviously this list is not conclusive. Typical compositions for hot melt pressure sensitive adhesives to be used are those prepared from between 10 and 100% by weight, preferably 20 to 80% by weight and in particularly preferred manner 20 to 50% by weight of polymer, between 10 and 80% by weight, preferably 15 to 60% by weight of plasticizer, between 10 and 80% by weight, preferably 15 to 60% by weight of tackifier, optionally 0.1 to 5% by weight of antiagers and optionally 0 to 70% by weight of fillers, the sum of the percentages of the components always being 100.

Preferably the hot melt pressure sensitive adhesive contains 10 to 50% by weight of styrene-isoprene-styrene synthetic rubber, such as is commercially available under the name CARIFLEX TR 1107 of SHELL, between 10 and 80% by weight of a hydrogenated alcohol, such as is commercially available under the name ABITOL from HERCULES, between 10 and 80% by weight of a hydrocarbon resin, e.g. HERCULES C from HERCULES, between 1 and 40% by weight of esters of vegetable fatty acids, e.g. MIGLYOL 812 of DYNAMIT NOBEL and optionally up to 5% by weight of antiagers, such as hydroquinone etc. as well as up to 70% by weight of fillers.

In a further preferred embodiment of the invention the hot melt pressure sensitive adhesive has 10 to 50% by weight of a polycaprolactone, e.g. CAPA 650 of INTEROX, between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, such as MIGLYOL 812 of DYNAMIT NOBEL and optionally up to 5% by weight of antiagers, as well as up to 70% by weight of fillers.

It can be advantageous for the hot melt pressure sensitive adhesive to have 10 to 50% by weight of polyethylene-vinyl acetate, such as EVATANE 28-25 of ATOCHEM, between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, e.g. MIGLYOL 812 of DYNAMIT NOBEL and optionally up to 5% by weight of antiagers, such as hydroquinone, etc. and up to 70% by weight of fillers.

A suitable hot melt pressure rensitive adhesive can contain up to 10 to 50% by weight of polyurethane, such as e.g. LUPHEN P 1110 of BASF, between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, e.g. MIGLYOL 812 of DYNAMIT NOBEL and optionally up to 5% by weight of antiagers, as well as up to 70% by weight of fillers.

It is also possible for the hot melt pressure sensitive adhesive to contain up to 10 to 50% by weight of polyamide, such as e.g. EURELON 930 of SCHERING, between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, e.g. MIGLYOL 812 of DYNAMIT NOBEL and optionally up to 5% by weight of antiagers, as well as up to 70% by weight of fillers.

It is also possible to use a hot melt pressure sensitive adhesive with 10 to 50% by weight of epoxide, e.g. EUREPOX 7001 of SCHERING, between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, e.g. MIGLYOL 812 of DYNAMIT NOBEL and optionally up to 5% by weight of antiagers, such as hydroquinone, etc., as well as up to 70% by weight of fillers.

Another hot melt pressure sensitive adhesive usable in the production of inventive transdermal systems has up to 10 to 50% by weight of polyisobutene with a tacky, rubber-like consistency, such as e.g. OPPANOL B 50 of BASF, between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, e.g. MIGLYOL 812 of DYNAMIT NOBEL and optionally up to 5% by weight of antiagers, as well as up to 70% by weight of fillers.

It is finally preferred to use hot melt pressure sensitive adhesives with a polyester base and which e.g. contain between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, e.g. MTGLYOL 812 of DYNAMIT NOBEL and optionally up to 5% by weight of antiagers, as well as up to 70% by weight of fillers.

Inventive apparatuses can also contain one or more substance depots, in which the substance is present in a higher concentration than the active substance-possessing hot melt pressure sensitive adhesive layer, so that higher substance doses can be processed and consequently the apparatus can remain in use longer before it has to be changed. Typical constructions appear e.g. in DE-OS 36 29 304. Preferred constructions of the invention are given in the subclaims, to which express reference is made.

BRIEF DESCRIPTION OF THE DRAWINGS

Further features and advantages of the invention are explained in greater detail hereinafter relative to the drawings, wherein show.

DESCRIPTION OF PREFERRED EMBODIMENTS

Figure 1:
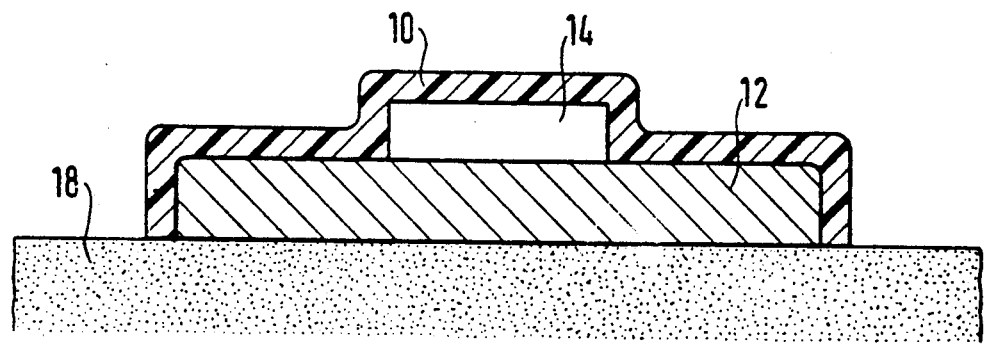
FIG. 1 a diagrammatically represented section through the layers of an inventive apparatus with a substance depot.

FIG. 1 shows an inventive apparatus, which is in this case in the form of a plaster-like, active substance-containing, transdermal, therapeutic system. It has a hot melt pressure sensitive adhesive layer 12, an active substance depot 14 in which the active substance has a higher concentration than in the hot melt pressure sensitive adhesive layer 12, as well as an active substance-impermeable carrier 10, on which rests the active substance depot 14 and which is stuck to the skin 18. Active substance now continuously migrates at a predetermined rate through the skin 18, so that the active substance content of layer 12 decreases. The active substance decrease is compensated by an after-flow of active substance from the active substance depot 14, so that over a predeterminable period of time there is an equilibrium concentration of the active substance in the hot melt contact adhesive layer 12, which ensures the delivery of a constant active substance quantity to the skin 18.

Figure 2:
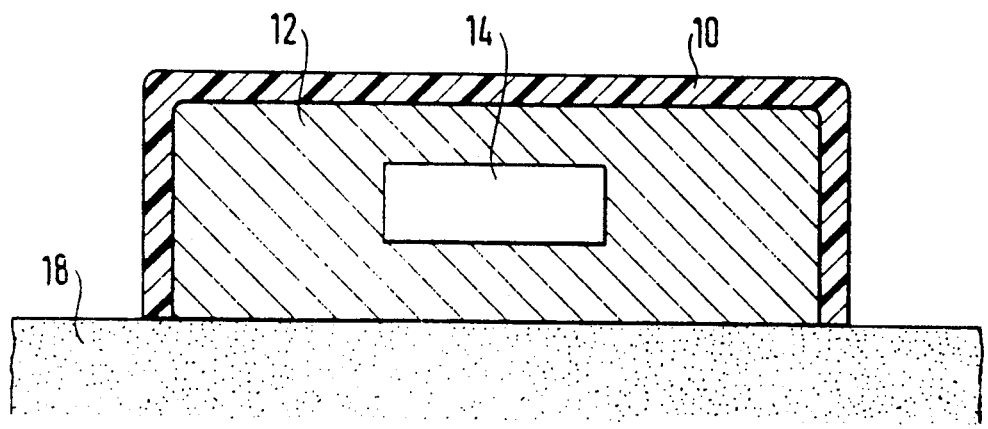
FIG. 2 a diagrammatically represented section through a further inventive apparatus with an active substance depot.

FIG. 2 shows another embodiment of an inventive apparatus, in which an active substance depot 14 is surrounded on all sides by the hot melt contact adhesive layer 12. This embodiment is particularly suitable if a large contact surface between the active substance depot and the hot melt contact adhesive layer is desired for a rapid active substance delivery to the hot melt contact adhesive layer.

Figure 3:
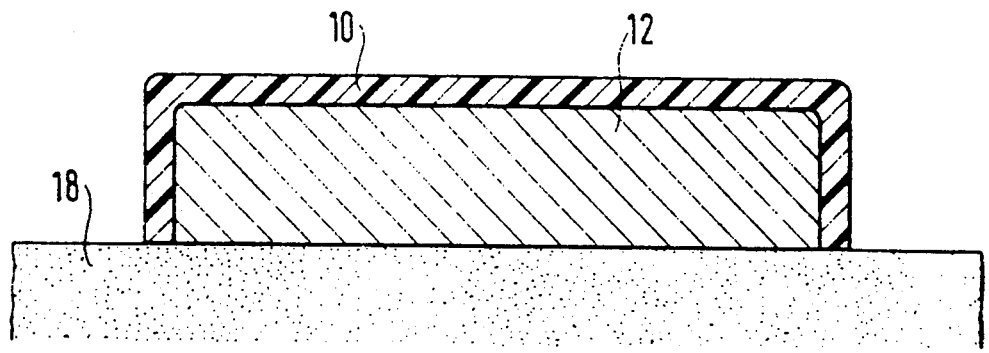
FIG. 3 a diagrammatically represented section through another embodiment of an inventive apparatus without a substance depot.

FIG. 3 shows a further simple embodiment of an inventive apparatus, in which an active substance-containing hot melt contact adhesive layer 12 is applied to an impermeable carrier material 10 in such a way that the latter covers the layer 12 on three sides. With the free hot melt contact adhesive surface it is stuck to the skin 18, so that a whole-area contact is ensured over the application time and the transfer of the active substance to the skin always takes place over a constant surface and at a constant speed.

The inventively improved production of an inventive apparatus will now described. Firstly the mixture of the components of the hot melt contact adhesive and the substance to be administered is prepared. This mixture is then brought to the processing temperature and then applied from the melt to a carrier material. The further processing, such as the application of an abhesively finished protective layer material take place in the conventional way.

What is claimed is:

1. Process for the production of an apparatus for the controlled transdermal release of an active substance consisting essentially of:

heating a hot melt pressure sensitive adhesive to a temperature in the range of about 40° to 80° C., introducing an active substance into the pressure sensitive adhesive to provide a reservoir for the distribution of the active substance, and applying the reservoir to a carrier to form the apparatus wherein the adhesive has a processing temperature in the range of about 40° to 80° C., and wherein the adhesive is without solvents.

2. The process according to claim 1, wherein the hot melt pressure sensitive adhesive comprises a polymer selected from the group consisting of styrene-isoprene-styrene block polymer, polycaprolactone, ethylene-vinylacetate copolymer, polyurethane, polyepoxide, polyisobutene and polyvinylether.

3. Process according to claim 1, wherein the processing temperature of the hot melt pressure sensitive adhesive is between 40 and 60 degree Celsius.

4. Process according to claim 1, wherein the processing temperature of the hot melt pressure sensitive adhesive is between 40 and 55 degrees Celsius.

5. Process according to claim 2 wherein the adhesive further includes a material selected from the group consisting of plasticisers, tackifiers, fillers, anti-agers and thixotropic agents.

6. Process according to claim 3, wherein the hot melt pressure sensitive adhesive is produced from between 10 to 80% by weight of polymer, between 10 to 80% by weight of plasticiser, and between 10 and 80% by weight of tackifier, whereas the sum of percentages is always 100.

7. Process according to claim 6, wherein the hot melt pressure sensitive adhesive includes between 20 to 80% by weight of polymer.

8. Process according to claim 6, wherein the hot melt pressure sensitive adhesive includes between 20 to 50% by weight of polymer.

9. Process according to claim 6, wherein the hot melt pressure sensitive adhesive is produced having 15 to 60% by weight of plasticiser.

10. Process according to claim 6, wherein the hot melt pressure sensitive adhesive includes 15 to 60% by weight of tackifier.

11. Process according to claim 6, wherein the hot melt pressure sensitive adhesive includes 0.1 to 5% by weight anti-agers.

12. Process according to claim 6, wherein the hot melt pressure sensitive adhesive includes 0 to 70% by weight of fillers.

13. Process according to claim 1, wherein the active substance containing hot melt pressure sensitive adhesive is applied at a temperature thereof between 45 to 55 degrees Celsius.

14. Process according to claim 1, and further including application of a protective layer material.

15. Process for the production of an apparatus according to claim 1, characterized by continuous or discontinuous application of active substance containing melted hot melt pressure sensitive adhesive at a temperature of the hot melt adhesive between 40 and 80 degrees Celsius onto a protective layer material.

16. Process according to claim 15, wherein the melted hot melt pressure sensitive adhesive is at a temperature between 40 and 60 degrees Celsius.

17. Process according to claim 15, wherein the melted hot melt pressure sensitive adhesive is at a temperature between 45 and 55 degrees Celsius.

18. Process according to claim 15, and further comprising applying a carrier so as to cover the apparatus.

19. Process for the production of an apparatus according to claim 15, wherein the formation of the components of the apparatus that contain hot melt pressure sensitive adhesive with a processing temperature of between 40 and 80 degrees Celsius is by a method selected from the group consisting of extrusion, pouring, roller application, knife coating, spraying, and pressing process.

20. The process according to claim 1, wherein the active substances to be released are temperature sensitive.

21. The process according to claim 1, wherein the active substances to be released are highly volatile.

22. An apparatus for the controlled release of active substances prepared according to the process of claim 1.

23. Apparatus according to claim 22, wherein the hot melt pressure sensitive adhesive having a distribution of active substance comprises at least one layer thereof.

24. Apparatus according to claim 22, and further comprising a detachable protective layer.

25. An apparatus for the controlled release of an active substance consisting essentially of a backing layer impermeable to the active substances and a hot melt pressure sensitive adhesive reservoir for distributing the active substance, wherein the reservoir has one or more parts, and wherein the apparatus is prepared according to the process consisting essentially of heating a hot melt pressure sensitive adhesive to a temperature in the range of about 40° to 80° C., introducing an active substance into the pressure sensitive adhesive to provide a reservoir for the distribution of the active substance, and applying the reservoir to the backing to form the apparatus for the controlled transdermal release of an active substance, wherein the adhesive has a processing temperature in the range of about 40° to 80° C., and wherein the adhesive is without solvents.

* * * * *

UNITED STATES PATENT AND TRADEMARK OFFICE
CERTIFICATE OF CORRECTION

PATENT NO. : 5,273,757
DATED : Dec. 28, 1993
INVENTOR(S) : Halvor Jaeger, Hans-Ranier Hoffmann, Reinhold Meconi, Robert-Peter Klein It is certified that error appears in the above-identified patent and that said Letters Patent is hereby corrected as shown below:

Column 8, line 67, after "melt" insert --pressure sensitive--.

Signed and Sealed this

Twenty-sixth Day of July, 1994

Attest:

BRUCE LEHMAN

*Attesting Officer*  *Commissioner of Patents and Trademarks*